United States Patent

Nübling et al.

[11] Patent Number: 5,872,296
[45] Date of Patent: Feb. 16, 1999

[54] SYNTHESIS OF OPTICALLY ACTIVE AMINOINDANOL

[75] Inventors: Christoph Nübling, Hassloch; Wolfgang Ladner, Fussgönheim, both of Germany

[73] Assignee: BASF Aktiengesellschaft, Ludwigshafen, Germany

[21] Appl. No.: 945,531

[22] PCT Filed: May 7, 1996

[86] PCT No.: PCT/EP96/01884

§ 371 Date: Oct. 28, 1997

§ 102(e) Date: Oct. 28, 1997

[87] PCT Pub. No.: WO96/35660

PCT Pub. Date: Nov. 14, 1996

[30] Foreign Application Priority Data

May 12, 1995 [DE] Germany .......................... 19517421.6

[51] Int. Cl.$^6$ .................................. C07C 213/02
[52] U.S. Cl. ................ 564/308; 564/182; 564/211; 564/428; 560/28
[58] Field of Search .................... 564/308, 428, 564/182, 211; 560/28

[56] References Cited

FOREIGN PATENT DOCUMENTS

| 95 07880 | 3/1995 | WIPO . |
| 95 0863 | 3/1995 | WIPO . |

OTHER PUBLICATIONS

Jr. of Med. Chem. Bd. 35, N4. 10, (1992).
Jr. of American Chem. Soc., Bd. 73, (1951).
Tetrahedron, Bd. 47, N4. 27, (1991).

*Primary Examiner*—Brian M. Burn
*Attorney, Agent, or Firm*—Keil & Weinkauf

[57] ABSTRACT

A process for preparing enantiomerically pure cis-1-amino-2-hydroxyindane, which comprises a) converting racemic trans-1-aminoindan-2-ol with acids or acid derivatives of the general formula RCOX by conventional methods into amides of type A

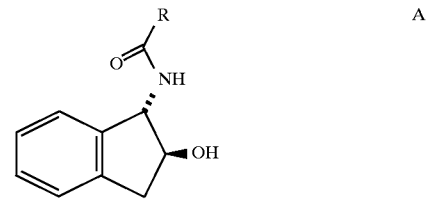

b) adding seed crystals of one enantiomer to a supersaturated solution or melt of the racemic amide A, c) isolating the crystals which have separated out, and again supersaturating the remaining mother liquor or melt after dissolving racemic amide A, and adding seed crystals of the other enantiomer, leading to selective crystallization of the latter, d) converting the resulting enantiomerically pure trans amide by conventional methods into the enantiomerically pure cis-1-amino-2-hydroxyindane.

10 Claims, No Drawings

SYNTHESIS OF OPTICALLY ACTIVE AMINOINDANOL (1S, 2R)-1-Aminoindan-2-ol (1) is an important intermediate for HIV protease inhibitors [1] I. Houpis et al., Tetrahedron Lett. 35 (1994) 9355; 2) B. Kim et al., Tetrahedron Lett. 35 (1994) 5153; 3) D. Askin et al., Tetrahedron Lett. 35 (1994) 673; 4) B. Dorsey et al., J. Med. Chem. 37 (1994) 3443; 5) EP 617968; 6) S. Young et al., J. Med. Chem. 35 (1992) 1702; 7) W. Thompson et al., J. Med. Chem. 35 (1992) 1685; 8) D. Askin et al., J. Org. Chem. 57 (1992) 2771; 9) J. Huff, J. Med. Chem. 34 (1991) 2305; 10) T. Lyle et al., J. Med. Chem. 34 (1991) 1228].

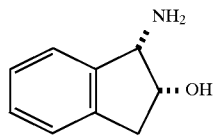

Various routes for synthesizing 1 have been described: racemic cis-1-aminoindan-2-ol can be prepared by isomerizing the corresponding trans compound which can be obtained in two stages from indene [C. Suter et al., J. Am. Chem. Soc. 62 (1940) 3473; Lit. Ref. 7)]. The racemate resolution was carried out by chromatography of the diastereomeric phenylalaninamides and hydrolysis thereof to 1 [Lit. Ref. 7)] or by crystallization of the diastereomeric tartrates [P. Reider (Merck & Co Inc) at the "Chiral '94" Congress (Reston/Virginia, USA)]. These methods have the disadvantage that derivatives are needed for costly chromatography or elaborate recycling of the tartaric acid is required.

DE 4332738.9 describes a process for resolving the racemates of cis- and trans-1-aminoindan-2-ol by enzymatic acylation, with only trans-1-aminoindan-2-ol being acylated with sufficient enantioselectivity. The resulting amide can be used directly for isomerization. The disadvantages of this method are the lack of chemical and thermal stability and the high cost of the enzymes.

Asymmetric epoxidation of indene [P. van Eikeren (Sepracor Inc.) at the "Chiral '94" Congress (Reston/Virginia, USA)] results in optically active indene epoxide (ee=86%), from which 1 can be obtained in a few stages. However, because the enantiomeric excess is insufficient, it is necessary in this case to enrich to ee>99.5%, which can be achieved by crystallizing the benzamide of trans-1-aminoindan-2-ol or of cis-1-aminoindan-2-ol tartrate. However, this process requires additional derivatization steps and recycling of the tartaric acid, and relatively large amounts of the epoxidation catalyst are needed.

Another possibility for preparing optically pure 1 was described by E. Didier et al. [Tetrahedron Lett. 27 (1991) 4941]. The crucial step is a diastereo- and enantioselective reduction of 1-methoxycarbonylindan-2-one with baker's yeast. However, this synthesis has many stages and gives low yields.

It is an object of the present invention to find a novel, low-cost method for preparing enantiomerically pure (1S, 2R)-1-aminoindan-2-ol (1).

Racemate resolution by crystallization is still the most widely used method for preparing pure enantiomers. If suitable functional groups are present, the resolution is usually effected by crystallizing diastereomeric salts. However, in certain cases, direct crystallization of one enantiomer is possible. The prerequisite for this is that a compound is, in the solid state, in the form of a conglomerate, i.e. a 1:1 mixture of the two enantiomers [review in: R. Sheldon, "Chirotechnology, industrial synthesis of optically active compounds", Dekker, 1993, page 173]. Direct crystallizations of this type are used, for example, in the preparation of chloramphenicol [P. Amiard, Experientia 15 (1959) 38] and α-methyl-L-dopa [D. Reinhold et al., J. Org. Chem. 33 (1968) 1209].

It is advantageous to resolve a racemate into the antipodes at the earliest possible stage of the synthesis in order to minimize the amount of superfluous ballast carried through the reaction sequence. With the exception of the multistage synthesis of Didier et al. (see above), all the other routes to 1 start from indene, which can easily be converted into trans-1-aminoindan-2-ol by epoxidation and opening of the epoxide with ammonia. To date (with the exception of the enzymatic process indicated in DE 4332738.9) no resolutions of racemates of trans-1-aminoindan-2-ol or derivatives thereof have been described.

We have now found, surprisingly, that the racemate resolution can be carried out at the stage of trans-1-aminoindan-2-ol by direct crystallization. For this purpose, the racemic amino alcohol 2 is converted with acids or acid derivatives of the general formula RCOX by conventional methods [Houben-Weyl, Methoden der organischen Chemie, Thieme 1985, vol. E5, pages 934 et seq.] into amides of type A.

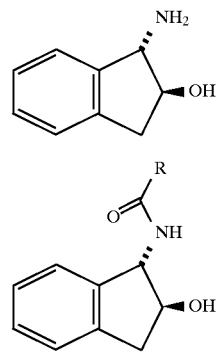

The substituent R has the following meanings: hydrogen, $C_1$–$C_6$-alkyl, $C_3$–$C_6$-cycloalkyl and phenyl, it being possible for these groups to carry one to three halogen atoms and/or one to three of the following radicals: cyano, $C_1$–$C_6$-alkoxy, $C_1$–$C_6$-alkylthio, phenyl, phenylthio and phenoxy, it being possible for the phenyl radicals in turn to carry one to three of the following groups: $C_1$–$C_4$-alkyl, $C_1$–$C_4$-alkoxy, halogen, cyano and nitro.

X is OH, halogen, $OR^1$ and $SR^1$, where $R^1$ is $C_1$–$C_6$-alkyl, phenyl and COR.

For the racemate resolution, seed crystals of the appropriate enantiomerically pure amide are added to a supersaturated solution or a melt of a racemic amide A, which induces the formation of crystals which contain a large excess of the seed crystal enantiomer. The crystals are filtered off and can easily be obtained in enantiomerically pure form by recrystallization. An amount of racemate A equivalent to the amount of crystals which has separated out is dissolved in the filtrate, which now contains an excess of the other enantiomer, by raising the temperature. The solution or melt is again supersaturated by cooling, and subsequently seed crysals of the other enantiomer are added, now making it possible for the latter to crystallize selectively. Repetition of these steps (dissolving the racemate in the filtrate, supersaturation and alternate crystallization of the two enantiomers by adding seed crystals) makes complete racemate resolution possible. Only at the start is it necessary to obtain the seed crystals in an independent way, which is possible, for example, by the enzymatic racemate resolution described in DE 4332738.9.

Another possibility for direct crystallization of a conglomerate is to pump a supersaturated solution of the racemate through two parallel crystallization vessels which contain seed crystals of in each case one of the two enantiomers on filter plates. Thus, part of one enantiomer crystallizes in one vessel, and part of the other crystallizes in the other vessel. The filtrates are combined and passed through a storage vessel which contains the conglomerate, where they are saturated again by heating. The saturated solution is supersaturated by cooling and passed anew into the crystallization vessels, thus completing the circulation [described by way of example in Chem. Eng. Nov. 8, 1965].

Suitable solvents are ethers such as tetrahydrofuran, dioxane, dimethoxyethane and diglycol dimethyl ether; $C_1$–$C_6$-alcohols such as methanol, ethanol, propanol, isopropanol, the isomeric butanols, the isomeric pentanols and hexanol; hydrocarbons such as toluene and xylene, and halogenated hydrocarbons such as methylene chloride, chloroform, dichloroethane and chlorobenzene. It is also possible to use mixtures of solvents. The process according to the invention can, however, also be carried out without using solvents in a crystal melt.

Amides of type A suitable and preferred for resolving racemates of trans-1-aminoindan-2-ol by direct crystallization are those where the radical R has the following meanings: $C_1$–$C_6$-alkyl and phenyl, it being possible for these groups to carry one to three halogen atoms and/or one to three of the following radicals: cyano, $C_1$–$C_6$-alkoxy, phenyl and phenoxy, it being possible for the phenyl radicals in turn to carry one to three of the following groups: $C_1$–$C_4$-alkyl, $C_1$–$C_4$-alkoxy, halogen, cyano and nitro.

Particularly preferred amides of type A are those where the radical R has the following meanings: $C_1$–$C_4$-alkyl, and phenyl, it being possible for these groups to carry one to three chlorine atoms and/or one to three of the following radicals: $C_1$–$C_4$-alkoxy, phenyl and phenoxy, it being possible for the phenyl radicals in turn to carry one to three of the following groups: $C_1$–$C_4$-alkyl, $C_1$–$C_4$-alkoxy, halogen, cyano and nitro. Particularly preferred examples are the benzamide 3, the methoxyacetamide 4, the phenylpropionamide 5 and the chloroacetamide 6.

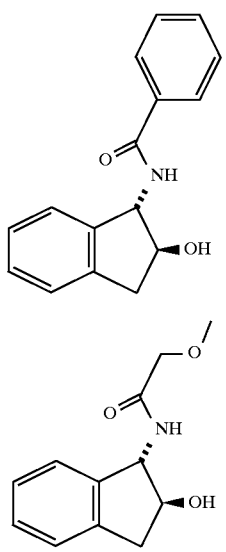

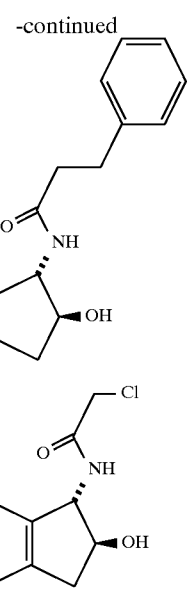

(1S, 2R)-1-Aminoindan-2-ol 1 is obtained from the (1S, 2S)-amides obtained by crystallization by reaction with thionyl chloride and acid hydrolysis of the resulting oxazolines [R. Lutz et al., J. Am. Chem. Soc. 73 (1951) 1639]. Thus, no additional derivatizations are necessary. It is possible and particularly advantageous to use the phenylpropionamide 5. The enantiomerically pure amide is converted by the above method with thionyl chloride into the corresponding oxazoline which is subjected to alkaline hydrolysis to give (1S, 2R)-1-phenyl-propionylamino-2-hydroxyindane. This compound is the stage following 1 in the synthesis of orally available HIV protease inhibitors (Lit. Ref. 3).

The concentration of the supersaturated solutions depends on the solvent, the temperature and the relative ratio of the two enantiomers. In alcoholic solvents it is typically 1–10% by weight.

The crystals resulting from the above process are filtered off, washed with cold solvent and dried. Virtually enantiomerically pure crystals of the two enantiomers (ee>99.5%) are obtained by a single recrystallization.

EXPERIMENTAL EXAMPLES

1) Crystallization of trans-1-methoxyacetamido-2-hydroxyindane a) Racemic trans-1-methoxyacetamido-2-hydroxyindane 4 (5 g) was dissolved by heating in isopropanol (100 ml) and slowly cooled until crystallization commenced (43° C.). It was again heated until the amide was completely dissolved (51° C.), and the solution was supersaturated by cooling to 49° C. At this temperature, seed crystals of the enantiomerically pure (1S, 2S)-1-methoxyacetamido-2-hydroxyindane (475 mg) were added and the mixture was slowly cooled while stirring to 45° C. The precipitate was filtered off with suction and washed with a little cold isopropanol.
Yield: 940 mg; ee=89.5%.

b) Racemic 4 (1 g) was added to the mother liquor from 1a), which was heated until the amide dissolved completely (60° C.). The solution was supersaturated by cooling to 52° C. and (1R, 2R)-1-methoxyacetamido-2-hydroxyindane (50 mg) was added, and the mixture was slowly cooled while stirring to 48° C. The precipitate was filtered off with suction and washed with a little cold isopropanol.
Yield: 310 mg; ee=95%.

We claim:
1. A process for preparing enantiomerically pure cis-1-amino-2-hydroxyindane, which comprises
   a) converting racemic trans-1-aminoindan-2-ol with acids or acid derivatives of the general formula RCOX by conventional methods into amides or carbamates of type A

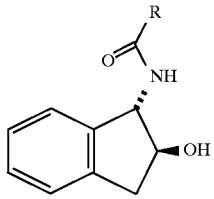

A where the substituents have the following meanings:
   R is hydrogen, $C_1$–$C_6$-alkyl, $C_3$–$C_6$-cycloalkyl, phenyl, $C_1$–$C_6$-alkoxy and phenoxy, it being possible for these groups to carry one to three halogen atoms and/or one to three of the following radicals: cyano, $C_1$–$C_6$-alkoxy, $C_1$–$C_6$-alkylthio, phenyl, phenylthio and phenoxy, it being possible for the phenyl radicals in turn to carry one to three of the following groups: $C_1$–$C_4$-alkyl, $C_1$–$C_4$-alkoxy, halogen, cyano and nitro,
   X is OH, halogen, $OR^1$ and $SR^1$, where $R^1$ is $C_1$–$C_6$-alkyl, phenyl and COR,
   b) adding seed crystals of one enantiomer to a supersaturated solution or melt of the racemic amide or carbamate A,
   c) isolating the crystals which have separated out, and again supersaturating the remaining mother liquor or melt after dissolving racemic amide or carbamate A, and adding seed crystals of the other enantiomer, leading to selective crystallization of the latter,
   d) converting the resulting enantiomerically pure trans amide or carbamate by conventional methods into the enantiomerically pure cis-1-amino-2-hydroxyindane.

2. A process as claimed in claim 1, wherein the radical R has the following meanings: $C_1$–$C_6$-alkyl, phenyl, $C_1$–$C_6$-alkoxy and phenoxy, it being possible for these groups to carry one to three halogen atoms and/or one to three of the following radicals: cyano, $C_1$–$C_6$-alkoxy, phenyl and phenoxy, it being possible for the phenyl radicals in turn to carry one to three of the following groups: $C_1$–$C_4$-alkyl, $C_1$–$C_4$-alkoxy, halogen, cyano and nitro.

3. A process as claimed in claim 1, wherein the radical R has the following meanings: $C_1$–$C_4$-alkyl, phenyl, $C_1$–$C_4$-alkoxy and phenoxy, it being possible for these groups to carry one to three chlorine atoms and/or one to three of the following radicals: $C_1$–$C_4$-alkoxy, phenyl and phenoxy, it being possible for the phenyl radicals in turn to carry one to three of the following groups: $C_1$–$C_4$-alkyl, $C_1$–$C_4$-alkoxy, halogen, cyano and nitro.

4. A process as claimed in claim 1, wherein the radical R is phenyl, phenylethyl, chloromethyl, methoxymethyl, methoxy, phenoxy or benzyloxy.

5. trans-1-Phenylpropionylamino-2-hydroxyindane and the two enantiomers (1S, 2S)- and (1R, 2R)-1-phenylpropionylamino-2-hydroxyindane.

6. trans-1-Chloroacetylamino-2-hydroxyindane and the two enantiomers (1S, 2S)- and (1R, 2R)-1-chloroacetylamino-2-hydroxyindane.

7. trans-1-Methoxycarbonylamino-2-hydroxyindane and the two enantiomers (1S, 2S)- and (1R, 2R)-1-methoxycarbonylamino-2-hydroxyindane.

8. trans-1-Phenoxycarbonylamino-2-hydroxyindane and the two enantiomers (1S, 2S)- and (1R, 2R)-1-phenoxycarbonyl-amino-2-hydroxyindane.

9. trans-1-Benzyloxycarbonylamino-2-hydroxyindane and the two enantiomers (1S, 2S)- and (1R, 2R)-1-benzyloxycarbonyl-amino-2-hydroxyindane.

10. A process as claimed in claim 1, in which ethers, alcohols, aromatic hydrocarbons or halogenated hydrocarbons are used as solvents.

* * * * *